(12) United States Patent
Murthy et al.

(10) Patent No.: US 6,320,976 B1
(45) Date of Patent: Nov. 20, 2001

(54) COMPUTER-ASSISTED DIAGNOSIS METHOD AND SYSTEM FOR AUTOMATICALLY DETERMINING DIAGNOSTIC SALIENCY OF DIGITAL IMAGES

(75) Inventors: Sreerama K. V. Murthy, New Delhi (IN); Jianzhong Qian, Monmouth Junction, NJ (US); Carol L. Novak, Newton, PA (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/283,550

(22) Filed: Apr. 1, 1999

(51) Int. Cl.$^7$ .................................................. G06K 9/00
(52) U.S. Cl. ............................................................ 382/128
(58) Field of Search .................................. 382/128, 129, 382/131, 132, 133, 155, 159, 160, 181, 190, 195, 199, 203, 209, 210, 211, 215, 217, 218, 219, 220, 224, 225, 226, 227, 228, 232, 240, 260

(56) References Cited

U.S. PATENT DOCUMENTS

| | | | |
|---|---|---|---|
| 5,287,275 | * 2/1994 | Kimura | 707/5 |
| 5,680,485 | * 10/1997 | Loce et al. | 382/257 |
| 5,710,833 | * 1/1998 | Moghaddam et al. | 382/228 |
| 5,822,742 | * 10/1998 | Alkon et al. | 706/31 |
| 5,828,769 | * 10/1998 | Burns | 382/118 |
| 5,857,030 | * 1/1999 | Gaborski et al. | 382/132 |
| 5,870,493 | * 2/1999 | Vogl et al. | 382/195 |
| 5,923,779 | * 7/1999 | Ohmi et al. | 382/190 |
| 5,983,218 | * 11/1999 | Syeda-Mahmood | 770/3 |
| 6,058,206 | * 5/2000 | Kortge | 382/159 |
| 6,163,629 | * 12/2000 | Cheung et al. | 382/260 |

* cited by examiner

*Primary Examiner*—Andrew W. Johns
*Assistant Examiner*—Shervin Nakhjavan
(74) *Attorney, Agent, or Firm*—Donald B. Paschburg

(57) ABSTRACT

A computer-assisted diagnosis method and system are provided for automatically determining diagnostic saliency of digital images. The method includes the step of providing filters for evaluating the image. Each filter is designed to identify a specific type of diagnostic finding, and is associated with the following: a virtual window for defining regions in the image at which the filter is applied; a set of training image patches corresponding to typical appearances of the specific type of diagnostic finding; a distance measure between the training image patches and the regions in the image defined by the virtual window; and a feature set corresponding to the distance measure. The filters are applied to the image to compute distances between the regions in the image defined by the virtual window and the training image patches based on the distance measure and the feature set, for each of the plurality of filters. Regions in the image are ranked as corresponding to a particular type of diagnostic finding based the computed distances.

37 Claims, 3 Drawing Sheets

COMPUTER-ASSISTED DIAGNOSIS METHOD AND SYSTEM FOR AUTOMATICALLY DETERMINING DIAGNOSTIC SALIENCY OF DIGITAL IMAGES

BACKGROUND

1. Technical Field

The present invention relates generally to computer-assisted diagnosis (CAD) and, in particular, to a CAD method and system for automatically determining diagnostic saliency of digital images.

2. Background Description

Computer-assisted diagnosis is an important technology in many different clinical applications. However, one of the more prevalent clinical applications for computer-assisted diagnosis is in the detection of breast cancer in women. According to the American Cancer Society, breast cancer is the most common cancer among women, other than skin cancer. It is the leading cause of death among women aged 40 to 55. There are approximately 179,000 new cases of breast cancer in the United States each year and about 43,500 deaths from the disease.

While there are presently no means for preventing breast cancer, early detection of the disease prolongs life expectancy and decreases the likelihood of the need for a total mastectomy. Accordingly, the American Cancer Society recommends that all women aged 40 and older should have a mammogram every year.

Diagnostic images such as mammograms typically contain large, diagnostically unimportant regions. These regions may belong to the background or to body parts uninteresting for the purposes of the present study. A human diagnostician is able to quickly identify and focus only on diagnostically relevant patches in the image. Knowledge of relative diagnostic saliency of image regions can increase the effectiveness and efficiency of computer aided diagnosis (CAD) and other digital image processing.

When humans look at an image, certain locations in the image typically visually "stand out" from the rest. In medical images, however, diagnostically salient regions (i.e., image regions the content of which is likely to influence the outcome of diagnosis) can have visually insignificant appearances. Human diagnosticians learn by experience to recognize salient regions in diagnostic images. A medical image such as, for example, a mammogram, may contain background structures corresponding to healthy breast tissue. Accordingly, a trained, focused eye of a radiologist is needed to detect small lesions among these structures. However, a typical radiologist may be required to examine up to hundreds of mammograms on a daily basis, leading to the possibility of a missed diagnosis due to human error. Thus, it would be desirable and highly advantageous to have a CAD method and system for automatically determining diagnostic saliency of digital images.

A knowledge of the diagnostic saliency of regions in a digital image, in addition to guiding a human reader to the interesting portions of the image, is also useful for increasing the efficiency and effectiveness of many digital image processing methods. For example, image display can be improved by enhancing diagnostically salient regions, optionally using lesion-specific enhancement operators. Moreover, image matching (e.g., bilateral, temporal or interview change detection for mammograms), can be accomplished more robustly by de-emphasizing diagnostically unimportant regions. Also, higher compression ratios may be achieved for image storage or transmission, without the loss of diagnostic quality, by allotting more bits or storage for diagnostically salient regions than for non-salient regions. Additionally, computer-aided lesion detection methods will benefit from a knowledge of which portions of an image are more important. Further, a knowledge of the diagnostic saliency of image regions can help reduce false positive findings of automatic lesion detection methods. The preceding are but some of the many applications to which knowledge about diagnostic saliency of a digital image may be applied.

SUMMARY OF THE INVENTION

The present invention is directed to a computer-assisted diagnosis method and system for automatically determining diagnostic saliency of digital images.

In one aspect of the present invention, there is provided a computer assisted diagnosis system for automatically determining diagnostic saliency of regions in a digital image comprised of a plurality of pixels. The system includes: a memory unit, a plurality of filters stored in the memory unit, each of the plurality of filters designed to identify a specific type of diagnostic finding, and associated with a virtual window for defining regions in the image at which the filter is applied, a set of training image patches corresponding to typical appearances of the specific type of diagnostic finding, a distance measure between the training image patches and the regions in the image defined by the virtual window, and a feature set corresponding to the distance measure; and a processor for applying each of the plurality of filters to the image to compute distances between the regions in the image defined by the virtual window and the training image patches based on the distance measures and the feature sets, and ranking regions in the image corresponding to a particular type of diagnostic finding based on the computed distances.

In another aspect of the present invention, there is provided a computer assisted diagnosis method for automatically determining diagnostic saliency of locations in a digital image comprised of a plurality of pixels. The method includes the steps of: providing a plurality of filters for evaluating the image, wherein each of the plurality of filters is designed to identify a specific type of diagnostic finding, and is associated with a virtual window for defining regions in the image at which the filter is applied, a set of training image patches corresponding to typical appearances of the specific type of diagnostic finding, a distance measure between the training image patches and the regions in the image defined by the virtual window, and a feature set corresponding to the distance measure; applying the plurality of filters to the image to compute distances between the regions in the image defined by the virtual window and the training image patches based on the distance measure and the feature set, for each of the plurality of filters; and ranking regions in the image as corresponding to a particular type of diagnostic finding based the computed distances.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a computer-assisted diagnosis method and system for automatically determining diagnostic saliency of digital images. To facilitate a clear understanding of the present invention, illustrative examples are provided herein which describe the invention in applications directed to the detection of breast cancer (i.e., automatically determining diagnostic saliency of digital mammograms). However, the invention is not solely limited to applications including digital mammograms. It is to be appreciated that the invention may be used to automatically determine diagnostic saliency of digital images corresponding to any part of the body. Further, the method and system of the present invention may be applied to multiple images at a given time to concurrently determine and rank the diagnostic saliency of the regions in each of the multiple images. Moreover, the present invention is equally applicable to both two and three dimensional images, as well as digitized or digitally acquired images.

A general description of the present invention will now be given to introduce the reader to the concepts and advantages of the invention. Subsequently, more detailed descriptions of various aspects of the invention will be provided.

Figure 1:
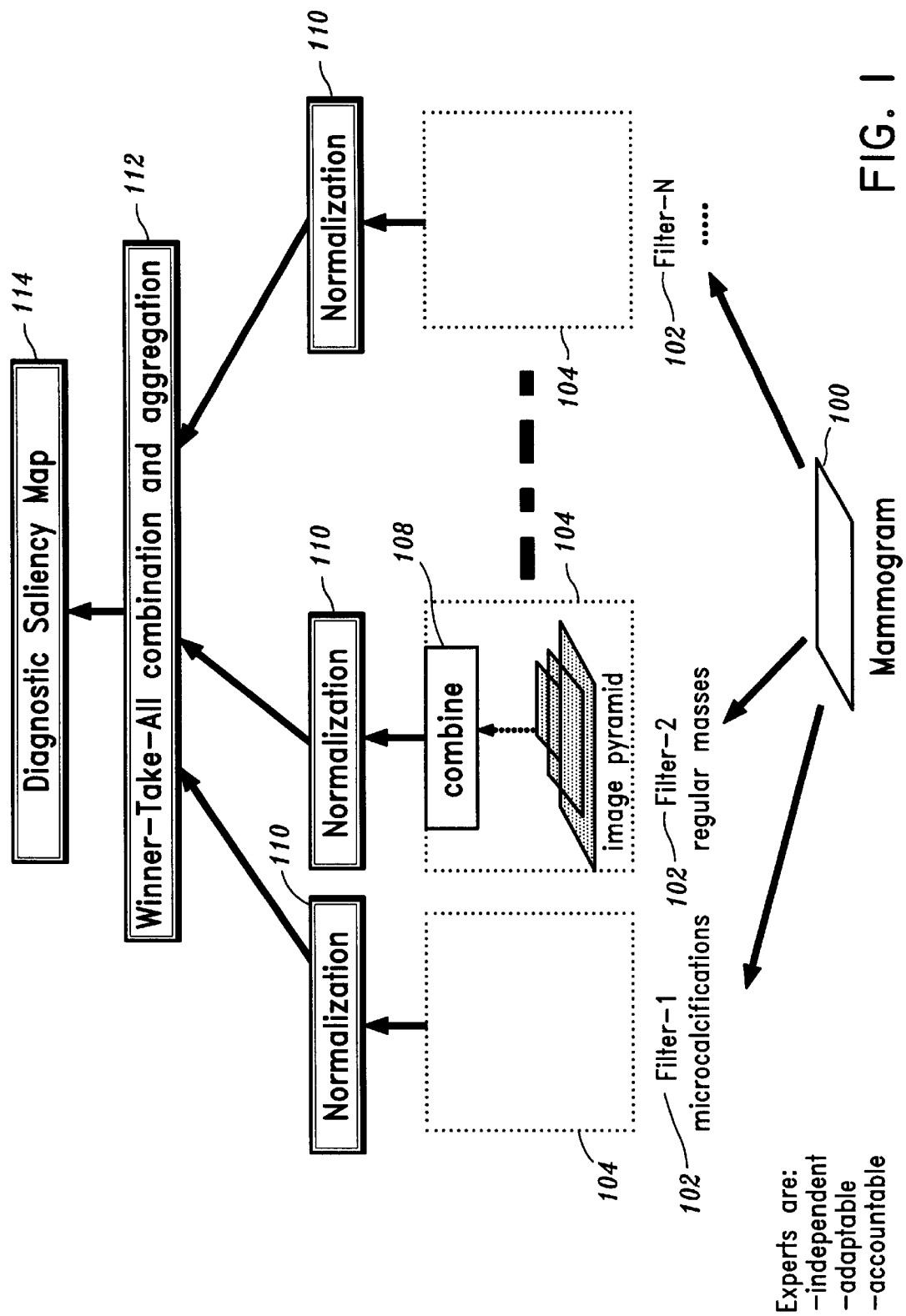
FIG. 1 is a diagram illustrating the generation of a diagnostic saliency map from a digital mammogram according to an embodiment of the present invention.

A general overview of the present invention is represented in FIG. 1, which is a diagram illustrating the generation of a diagnostic saliency map from a digital mammogram 100 according to an embodiment of the present invention.

In general, the invention identifies diagnostically salient regions (image regions the content of which is likely to influence the outcome of diagnosis) and provides a numeric diagnostic saliency score for image regions. The regions may then be ranked with or without accounting for specific disease characteristics (e.g., "indicate the top three regions in the image that look like microcalcifications" and "show all diagnostically salient regions at a sensitivity of 80%") that are predefined or contemporaneously defined by a user.

To these ends, the invention employs an expert architecture which includes disease-specific filters 102. A disease-specific filter is an algorithm designed to identify a specific type of diagnostic finding (e.g., well-bounded masses, stellar masses, microcalcifications, skin thickening, architectural distortions, etc.). It is to be appreciated that there may be more than one disease-specific filter for a specific type of diagnostic finding.

Each disease-specific filter is associated with a set of training image patches called an "oracle", a distance measure between image patches, and a feature set based on which distances are computed. Each training image patch in the oracle of a disease-specific filter corresponds to a "typical" appearance of the specific diagnostic finding the filter is designed to identify.

Each filter is applied at regions in the image defined by a virtual window 104 corresponding to the filter. For flexibility and adaptation, disease-specific filters are modeled as nearest neighbor classifiers. The response of a disease-specific filter to a particular region in the image defined by the virtual window associated with that filter is determined by computing the distance of the particular region to the closest training image patch in the oracle of the filter. Such response is inversely proportional to the distance between the region in the image defined by the virtual window and the closest training image patch in the set of training image patches. Distances are computed in a scale-, translation-, and rotation- independent manner, unless such dependence is warranted for the diagnostic finding in question. Each disease-specific filter uses a private set of features and a distance measure tailored to the specific diagnostic finding it is trying to isolate. It is often undesirable to measure distance between two image patches using just the pixel intensities. This is because the appearance, position, contrast and directionality of the same diagnostic findings can vary from image to image. In order to achieve shift-, rotation- and contrast- invariant distance computation, the disease-specific filters first translate each image patch into a set of invariant features. Specific feature sets used for particular diseases are described hereinbelow. Each image patch then becomes a point in this feature space, and distances are measured in the feature space. Features used for distance computation may or may not have diagnostic significance, and need not be comprehensible to a physician. That is, these are "private" to the disease-specific filter.

A disease-specific filter has built into it the knowledge of what image resolution it should be applied at. Based on the possible size variations of the diagnostic findings, some filters (e.g., for microcalcifications) are applied at a single resolution whereas some other (e.g., masses) are applied at multiple resolutions and the results are aggregated 108. For some filters (e.g., microcalcification), it is important to take into account the physical size of the pixel, so that lesions of a certain size (e.g., less than or equal to 1 mm) can be targeted irrespective of what physical resolution the image is taken at.

The outputs of the disease-specific filters are combined using normalization 110 so as to retain only the significant, non-noisy peaks. The normalization procedure also ensures that outputs of different filters are uniformly comparable to each other.

The outputs of the disease-specific filters may be used individually or may be combined into a "diagnostic saliency map" 114. In the latter case, such a combination is done using winner-take-all operators between image locations, and aggregation and/or winner-take-all operators between different disease-specific filters 112. The outputs of the filters are useful for such diverse purposes as, for example, image enhancement, change detection, and image compression.

Figure 2:
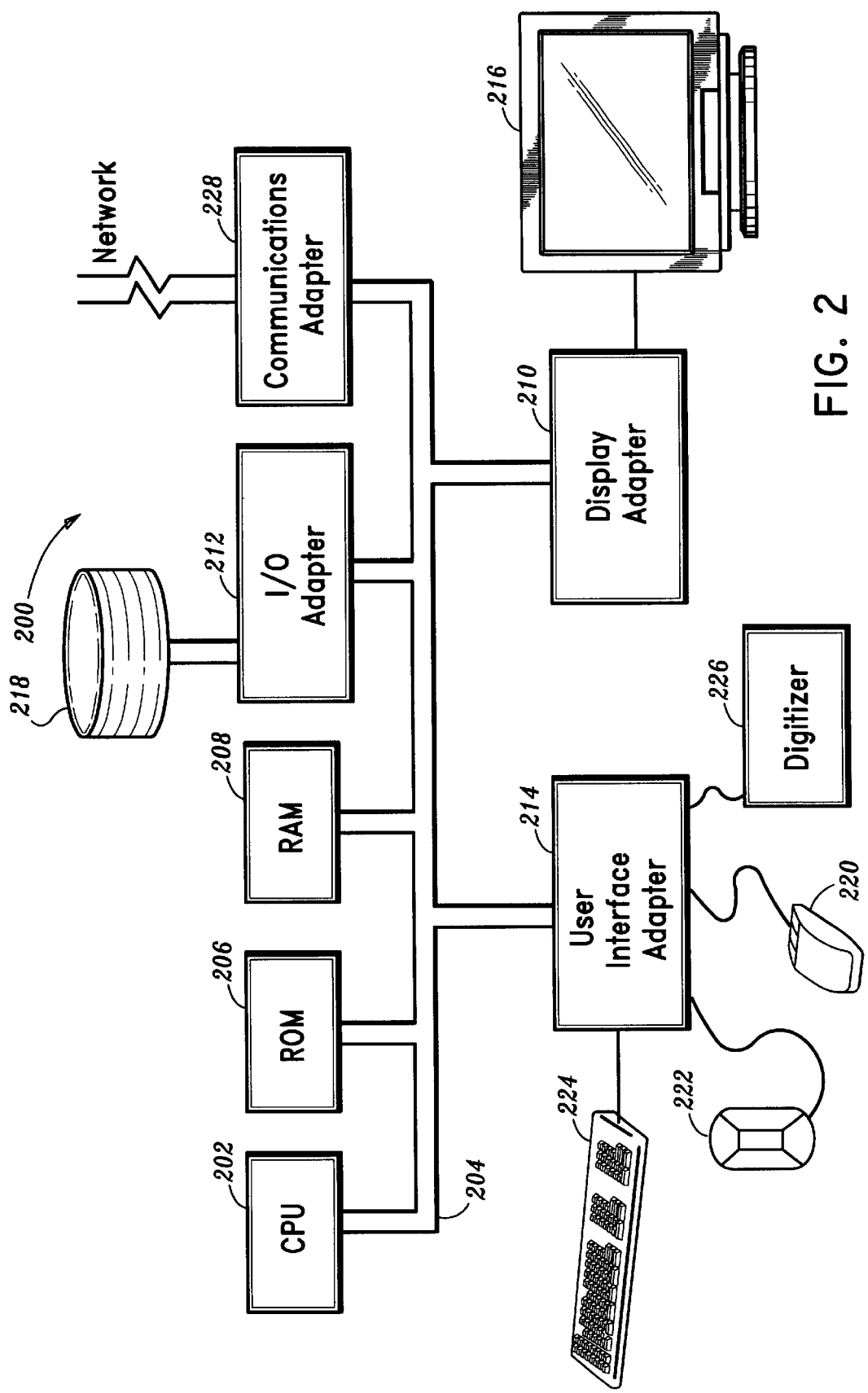
FIG. 2 is a block diagram of a computer-assisted diagnosis (CAD) system for automatically determining diagnostic saliency of digital images according to an embodiment of the present invention.

FIG. 2 is a block diagram of a computer-assisted diagnosis (CAD) system for automatically determining diagnostic saliency of digital images according to an embodiment of the present invention. The CAD system 200 includes at least one processor (hereinafter processor) 202 operatively coupled to other components via a system bus 204. A read only memory (ROM) 206, a random access memory (RAM) 208, a display adapter 210, an I/O adapter 212, and a user interface adapter 214 are operatively coupled to system bus 204.

A display device 216 is operatively coupled to system bus 204 by display adapter 210. A disk storage device (e.g., a magnetic or optical disk storage device) 218 is operatively couple to system bus 204 by I/O adapter 212.

A mouse 220, eye tracking device 222, and keyboard 224 are operatively coupled to system bus 204 by user interface adapter 214. The mouse 220, eye tracking device 222, and keyboard 224 are used to input and output information to and from CAD system 200. Moreover, eye tracking device 222 may be used for physician training and self-assessment as described hereinbelow.

The CAD system 200 may also include a digitizer 226 operatively coupled to system bus 204 by user interface adapter 214 for digitizing a developed x-ray diagnostic image. Alternatively, digitizer 226 may be omitted, in which case a digital diagnostic image may be input to CAD system 200 from a network via a communications adapter 228 operatively coupled to system bus 204.

The CAD system 200 also includes disease-specific filter modules 230 which are software modules that may be stored in any of the above memories. The disease-specific filter modules 230 may be stored in any arrangement in the above memories. For example, they may be initially stored in disk storage device 218 and then moved to RAM 208 upon startup of the system. Alternatively, a cache (not shown) may be employed to store the disease-specific filter modules.

The processor 202 applies each disease-specific filter at regions in the image defined by a virtual window corresponding to the filter. The size of the virtual window corresponding to a particular filter depends upon the diagnostic finding the filter is designed to isolate. The size of the window may be predefined with respect to a particular diagnostic finding. Alternatively, the size of the window may be dynamically determined by the system or the system user. The virtual window may be of any shape including, but not limited to, square, rectangular, circular, elliptical, and polygonal.

Two important characteristics of the disease-specific filters are adaptability and accountability. Adaptability results from the fact that training image patches may be added or deleted from the oracles, influencing their future response. Accountability means that for any response outputted by a disease-specific filter, the corresponding training image patch upon which the response was based may be presented to the user.

Further, new disease-specific filters may be added or existing filters may be removed at any time. For example, a filter bank designed to work with digitized mammograms can be augmented to also be effective with digitally acquired mammograms or spot mammograms. Moreover, the architecture of the present invention allows for "plugging in" third-party algorithms as disease-specific filters.

Figure 3:
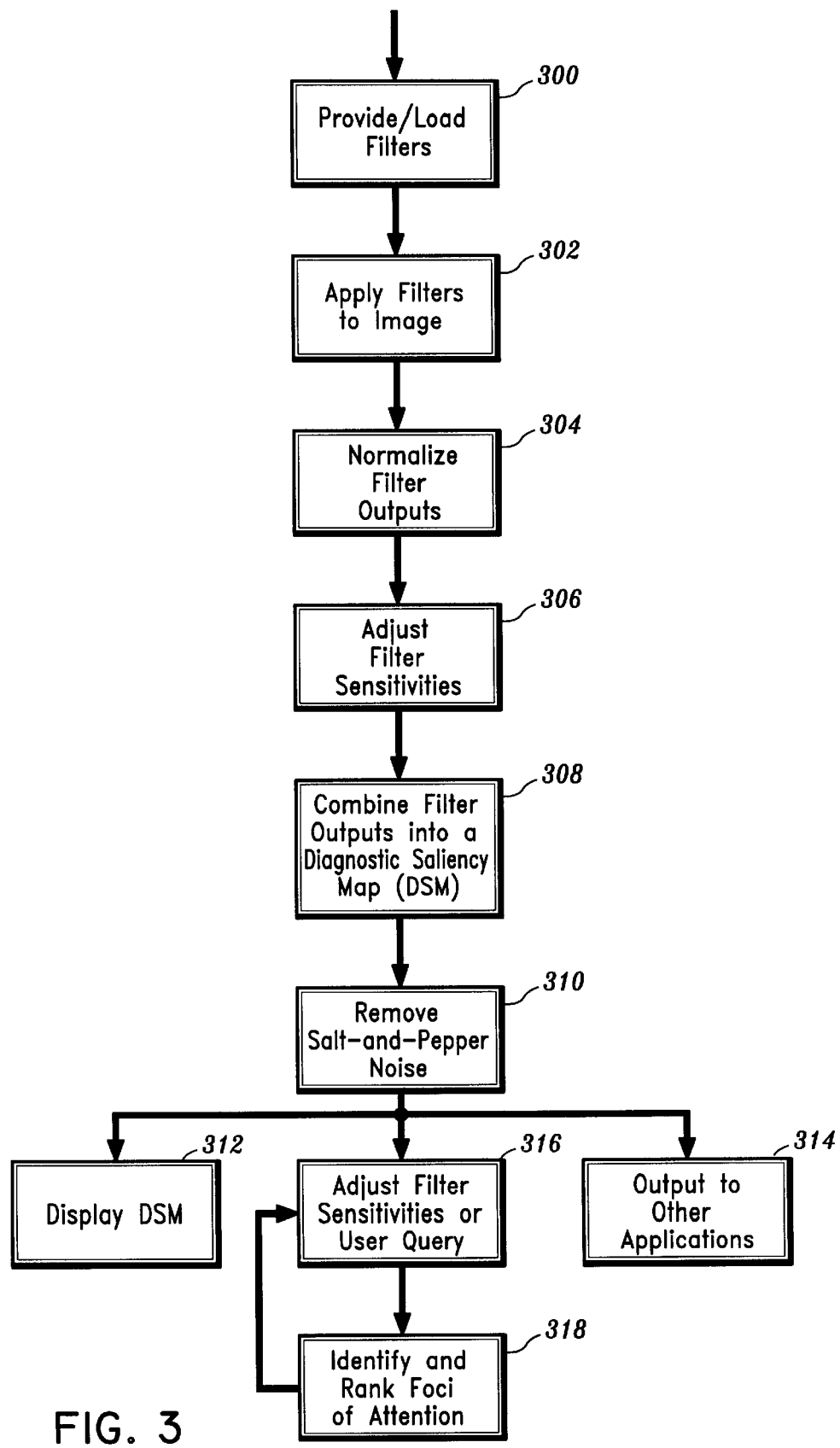
FIG. 3 is a flowchart of a computer-assisted diagnosis (CAD) method for automatically determining diagnostic saliency of digital images according to an embodiment of the present invention.

FIG. 3 is a flowchart of a computer-assisted diagnosis (CAD) method for automatically determining diagnostic saliency of digital images according to an embodiment of the present invention. In particular, the method is applicable to the system of FIG. 2.

Initially, a plurality of filters for evaluating the image are provided (e.g., loaded) (step 300). Each filter is designed to identify a specific type of diagnostic finding. Further, each filter is associated with the following: a virtual window defining a region in the image at which the filter is applied; a set of training image patches corresponding to typical appearances of the specific type of diagnostic finding; a distance measure between the training image patches and the regions in the image defined by the virtual window; and a feature set to be used in the distance computation.

Each disease-specific filter is applied to the image by processor 202 to compute distances from the regions in the image defined the virtual window corresponding to the filter to the training image patches in the oracle of the filter based on the distance measure and the feature set (also associated with that filter) (step 302). Preferably, processor 202 simultaneously applies each disease-specific filter so as to evaluate each pixel in the image. However, it is to be appreciated that the order in which the filters are applied to the pixels in not important. Thus, the filters may also be applied sequentially, randomly, or in any other order. Moreover, it is to be further appreciated that the filters need not be applied at all pixels in an image. For example, a pre-processing filter may be used to mask non-breast areas in a digital image. In such a case, the disease-specific filters need only be applied at the non-masked areas.

The disease-specific filters are associated with shift, rotation, and contrast invariant metrics for measuring distance between image patches. Specific implementations vary depending on the type of diagnostic finding the filter is attempting to isolate, and other factors. It is to be appreciated that multiple disease-specific filters designed to identify the same diagnostic finding may use different distance measures. For illustrative purposes, two possible distance metrics are described below, one for microcalcifications and the other for stellate masses. However, one skilled in the art may construct other distance metrics within the spirit and scope of the present invention.

A microcalcification is characterized by a set of pixels in the image which are substantially brighter than the background of the image and the geometric configuration of the set of pixels. Informally, two image patches with microcalcifications may be considered similar if they have a similar number of microcalcifications, in similar shaped clusters. An adaptive thresholding scheme first identifies pixels in the patch that are potential microcalcifications. For the calcification pixels, the convex hull around the pixels is computed. Distance between two image patches is a weighted summation of the difference in the number of calcifications and the distance between the cluster shapes. The distance between two cluster shapes is the minimal sum of distances between corresponding vertices of the convex hulls, after centering both hulls at (0,0).

A stellate mass is characterized by an optional central mass, and a set of rays emanating from the center in different directions. Informally, two stellate masses may be considered similar if their central masses are of the same size and shape, and the rays are similar in number and direction. A feature vector for distance computations between stellate mass image patches can include the number of pixels in the central mass, the number of vertices along the boundary of the central mass, the number of rays emanating from the center of the mass, the histogram of ray sizes, the histogram of ray directions, etc. The distance between two stellate mass image patches is then a weighted sum of the differences between corresponding features.

Next, the filter outputs, which include the computed distances, are normalized (step 304). This is performed so that filter outputs are comparable with each other. Normalization is also applied across the filters so as to dampen filters that produce many local maxima per image. This normalization can be used to increase the specificity of the disease-specific filter bank to be comparable to that of the most specific disease-specific filter.

The sensitivity of the filters may be adjusted as required (step 306). For example, the sensitivity of all the filters may be uniformly changed. Alternatively, different sensitivity levels may be assigned to different filters. Such changes and/or assignments may be made using a "slider". The slider may be a physical switch actuated by a user or it may be a visual switch in a graphical user interface (GUI) actuated by movement of, for example, mouse 220. The changes and/or assignments may also be made using keyboard 224.

The outputs of all the disease-specific filters are then combined into a single "diagnostic saliency map" (DSM) for the image (step 308). Such a combination is done using winner-take-all operators between image locations, and aggregation and/or winner-take-all operators between different disease-specific filters. Post-processing may be applied after aggregating different filter responses, to remove salt-and-pepper type of noise (step 310).

The diagnostic saliency map may then be displayed to a user (step 312). The diagnostic saliency map contains a numeric diagnostic saliency score for each location (pixel or groups of pixels) in the image, the type of diagnostic finding (e.g., masses) at that location, and specific characteristics (size, shape, etc.) of the finding. The scores may correspond to a pixel or a group of pixels. In a preferred embodiment, the scores correspond to the image regions defined by virtual windows.

Moreover, the output of the filters may be output from system 200 for use in other applications as described hereinbelow (step 314). Such output may include individual filter responses or the diagnostic saliency map for the image.

Furthermore, if desired, the sensitivity of the filters may be adjusted and/or a user query (step 316). Queries of the type "indicate the top three regions in the image that look like microcalcifications" and "show all diagnostically salient regions at a sensitivity of 80%" may be used. The queries may be provided to system 200 via, for example, keyboard 224. Alternatively, predefined queries may be provided to a user via display device 216, in which case the user may select a query using mouse 220 and/or keyboard 224.

Using the diagnostic saliency map, diagnostic foci of attention in a mammogram at a given level of sensitivity can be readily identified and ranked (step 318). Upon identifying and ranking the diagnostic foci of attention, a return is made to step 316 to allow the user to adjust the sensitivity of the filters as he or she desires.

Furthermore, the proposed architecture provides a means for effectively combining top-down guidance with bottom-up image analysis. Domain knowledge rules such as "well-bounded masses are 20% more likely to appear in upper left quadrant of the breast than in other quadrants" (hypothetical) can be integrated into the system through the normalization procedures of individual filters or while forming the diagnostic saliency map.

Knowledge about diagnostic foci of attention is useful for many purposes. For example, such knowledge may be used in computer aided enhancement of diagnostically salient regions. Each expert can be made to include a suite of enhancement filters. At an operator's request, appropriate enhancement operators may be selected and applied based on the specific characteristics of the diagnostic finding and applied.

Another exemplary application which could use knowledge about diagnostic foci of attention is change detection between pairs of mammograms. It is to be appreciated that comparisons based on diagnostically salient regions are potentially more robust than comparisons based on the entire image content, because diagnostically unimportant structures are de-emphasized in the matching.

Yet another exemplary application which could use knowledge about diagnostic foci of attention is image compression. By allocating more bits to the diagnostically salient regions than the background, better compression ratios can be achieved without compromising on image quality for diagnosis.

Still another exemplary application which could use knowledge about diagnostic foci of attention is physician training and self-assessment. Oracles formed by expert mammographers can be used to automatically determine foci of attention for a particular image. The actual foci of attention for inexperienced mammographers may be measured with devices that track eye gaze. By comparing these sets of foci, the system can indicate to the human what salient regions he/she may have missed to look at.

Although the illustrative embodiments have been described herein with reference to the accompanying drawings, it is to be understood that the present system and method is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A computer assisted diagnosis system for automatically determining diagnostic saliency of regions in a digital image comprised of a plurality of pixels, the system comprising:
   a memory unit;
   a plurality of filters stored in said memory unit, each of the plurality of filters designed to identify a specific type of diagnostic finding;
   a virtual window for defining regions in the image at which each of the plurality of filters is applied;
   a set of training image patches corresponding to typical appearances of the specific type of diagnostic finding;
   a distance measure set corresponding to the training image patches and the regions in the image defined by the virtual window;
   a feature set corresponding to the distance measure set; and
   a processor for applying each of the plurality of filters to the image to compute distances between the regions in the image defined by the virtual window and the training image patches bases on the distance measure set and the feature set, and ranking regions in the image corresponding to a particular type of diagnostic finding based on the computed distances.

2. The system according to claim 1, wherein said processor applies each of the plurality of filters so as to evaluate each of the plurality of pixels.

3. The system according to claim 1, wherein a response of a filter is inversely proportional to a distance between a region in the image defined by the virtual window and a closest training image patch in the set of training image patches.

4. The system according to claim 1, wherein said processor applies some of the plurality of filters to a multi-resolution image pyramid constructed from the image, and aggregates results between pyramid levels.

5. The system according to claim 1, wherein said processor normalizes outputs of each of the plurality of filters.

6. The system according to claim 1, further comprising an adjusting device for one of uniformly and independently adjusting a sensitivity of each of the plurality of filters.

7. The system according to claim 1, wherein said processor identifies and ranks foci of attention belonging to a particular type of diagnostic finding using individual filter responses.

8. The system according to claim 1, wherein said processor combines outputs of the plurality of filters into a single diagnostic saliency map for the image.

9. The system according to claim 8, wherein said processor combines the outputs of the plurality of filters using winner-take-all operators between the regions in the image defined by the virtual windows, and one of aggregation operators and winner-take-all operators between different filters.

10. The system according to claim 8, wherein the diagnostic map comprises a numeric diagnostic saliency score for each of the regions in the image defined by the virtual windows associated with the plurality of filters, the specific type of diagnostic finding at each of the regions and characteristics of the diagnostic finding.

11. The system according to claim 8, wherein said processor identifies and ranks diagnostic foci of attention in the image at a given level of sensitivity, using the diagnostic saliency map.

12. The system according to claim 1, wherein said processor generates a numeric diagnostic saliency score for the regions in the image defined by the virtual windows associated with the plurality of filters.

13. The system according to claim 1, wherein said processor pre-processes each of the training image patches in each set of training image patches to optimize a time for distance computation with a region in the image defined by the virtual window.

14. The system according to claim 1, wherein said processor removes salt-and-pepper type of noise from outputs of the filters.

15. The system according to claim 1, wherein said processor identifies an individual training image patch based on an output of the individual training image patch.

16. The system according to claim 1, wherein said processor integrates domain knowledge rules into one of normalizing outputs of the plurality of filters and generating a diagnostic saliency map for the image.

17. The system according to claim 1, wherein said distance measure set is specific to the specific type of diagnostic finding identified by said plurality of filters.

18. The system according to claim 1, wherein said feature set is specific to the specific type of diagnostic finding identified by the plurality of filters.

19. The system according to claim 1, wherein at least some of said plurality of filters are specific to at least one predetermined resolution of the digital image.

20. The system according to claim 1, wherein each of said plurality of filters is disease specific.

21. The system according to claim 1, wherein the digital image is a digital mammogram and the specific type of diagnostic finding corresponds to breast cancer.

22. A computer assisted diagnosis method for automatically determining diagnostic saliency of locations in a digital image comprised of a plurality of pixels, the method comprising the steps of:
providing a plurality of filters for evaluating the image, wherein each of the plurality of filters is designed to identify a specific type of diagnostic finding;
providing a virtual window for defining regions in the image at which each of the plurality of filters is applied;
providing a set of training image patches corresponding to typical appearances of the specific type of diagnostic finding;
providing a distance measure set corresponding to the training image patches and the regions in the image defined by the virtual window;
providing a feature set corresponding to the distance measure set;
applying the plurality of filters to the image to compute distances between the regions in the image defined by the virtual window and the training image patches based on the distance measure set and the feature set, for each of the plurality of filters; and
ranking regions in the image as corresponding to a particular type of diagnostic finding based the computed distances.

23. The method according to claim 22, wherein said applying step applies each of the plurality of filters so as to evaluate each of the plurality of pixels.

24. The method according to claim 22, wherein a response of a filter is inversely proportional to a distance between a region in the image defined by the virtual window and a closest training image patch in the set of training image patches.

25. The method according to claim 22, further comprising the step of pre-processing each of the training image patches in each set of training image patches to optimize a time for distance computation with a region in the image defined by the virtual window.

26. The method according to claim 22, further comprising the steps of:
constructing a multi-resolution image pyramid from the image;
applying some of the plurality of filters to the multi-resolution image pyramid; and
aggregating results between pyramid levels for each filter.

27. The method according to claim 22, further comprising the step of normalizing outputs of each of the plurality of filters.

28. The method according to claim 22, further comprising the step of adjusting sensitivities of the plurality of filters to be one of uniform and independent.

29. The method according to claim 22, further comprising the steps of identifying and ranking foci of attention belonging to a particular type of diagnostic finding using individual filter responses.

30. The method according to claim 22, further comprising the step of combining outputs of the plurality of filters into a single diagnostic saliency map for the image.

31. The method according to claim 22, further comprising the steps of identifying and ranking diagnostic foci of attention in the image at a given level of sensitivity, using the diagnostic saliency map.

32. The method according to claim 22, further comprising the step of combining the outputs of the plurality of filters using winner-take-all operators between the regions in the image defined by the virtual windows, and one of aggregation operators and winner-take-all operators between different filters.

33. The method according to claim 22, further comprising the step of removing salt-and-pepper type of noise from outputs of the filters.

34. The method according to claim 22, further comprising the step of generating a numeric diagnostic saliency score for the regions in the image defined by the virtual windows associated with the plurality of filters based on the computed distances.

35. The method according to claim 22, further comprising the step of combining outputs of the plurality of filters into a single diagnostic saliency map for the image, the map comprising a numeric diagnostic saliency score for each of the regions in the image defined by the virtual windows associated with the plurality of filters, the specific type of diagnostic finding at each of the regions and characteristics of the diagnostic finding.

36. The method according to claim 22, further comprising the step of identifying an individual training image patch based on an output of the individual training image patch.

37. The method according to claim 22, further comprising the step of integrating domain knowledge rules into one of normalizing outputs of the plurality of filters and generating a diagnostic saliency map for the image.

* * * * *